(12) United States Patent
Lu et al.

(10) Patent No.: US 10,722,475 B2
(45) Date of Patent: Jul. 28, 2020

(54) STEALTH NANOCAPSULES FOR PROTEIN DELIVERY

(71) Applicant: THE REGENTS OF THE UNIVERSITY OF CALIFORNIA, Oakland, CA (US)

(72) Inventors: Yunfeng Lu, Culver City, CA (US); Yang Liu, Los Angeles, CA (US); Jing Wen, Culver City, CA (US); Gan Liu, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/531,356

(22) PCT Filed: Nov. 20, 2015

(86) PCT No.: PCT/US2015/061838
§ 371 (c)(1),
(2) Date: May 26, 2017

(87) PCT Pub. No.: WO2016/085808
PCT Pub. Date: Jun. 2, 2016

(65) Prior Publication Data
US 2017/0354613 A1    Dec. 14, 2017

Related U.S. Application Data

(60) Provisional application No. 62/084,887, filed on Nov. 26, 2014.

(51) Int. Cl.
*A61K 9/51*    (2006.01)
*A61K 47/34*    (2017.01)
(Continued)

(52) U.S. Cl.
CPC ............ *A61K 9/513* (2013.01); *A61K 9/51* (2013.01); *A61K 47/34* (2013.01); *A61K 47/58* (2017.08);
(Continued)

(58) Field of Classification Search
None
See application file for complete search history.

(56) References Cited

U.S. PATENT DOCUMENTS 9,283,194 B2    3/2016 Tang et al.
9,993,440 B2    6/2018 Lu et al.
(Continued)

FOREIGN PATENT DOCUMENTS

EP    2260873    12/2010
EP    2260873 A1 * 12/2010 ........... A61K 47/543
(Continued)

OTHER PUBLICATIONS

Yan et al., "Encapsulation of Singe Enzyme in Nanogel with Enhanced Biocatalytic Activity and Stability", J Amer Chem Soc 128: 11008-11009 (2006) (Year: 2006).*
(Continued)

*Primary Examiner* — Aradhana Sasan
(74) *Attorney, Agent, or Firm* — Gates & Cooper LLP (57) ABSTRACT

The invention relates to methods and materials for extending a circulating half-life of a protein. The method comprises conjugating a protein with a polymerizable acryloyl group and encapsulating the protein with a layer of poly(2-methacryloxyloxyethyl phosphorycholine) (pMPC). The layer of pMPC comprises a plurality of 2-methacryloxyloxyethyl phosphorycholine monomers (MPC) polymerized with a N,N'-methylenebisacrylamide (BIS) crosslinker.

17 Claims, 7 Drawing Sheets

(51) Int. Cl.
  *A61K 48/00*    (2006.01)
  *C09D 4/00*     (2006.01)
  *C08F 230/02*   (2006.01)
  *C08L 33/04*    (2006.01)
  *A61K 47/69*    (2017.01)
  *A61K 47/58*    (2017.01)
  *B82Y 5/00*     (2011.01)

(52) U.S. Cl.
  CPC .......... *A61K 47/6925* (2017.08); *A61K 48/00* (2013.01); *C08F 230/02* (2013.01); *C08L 33/04* (2013.01); *C09D 4/00* (2013.01); *B82Y 5/00* (2013.01)

(56) References Cited

U.S. PATENT DOCUMENTS

| | | |
|---|---|---|
| 2014/0134700 A1 | 5/2014 | Lu et al. |
| 2014/0248212 A1 | 9/2014 | Radu et al. |
| 2015/0320693 A1 | 11/2015 | Lu et al. |

FOREIGN PATENT DOCUMENTS

| | | | |
|---|---|---|---|
| WO | 2007/100902 | 9/2007 | |
| WO | 2008/098930 | 8/2008 | |
| WO | WO-2013033717 A1 * | 3/2013 | ............... A61K 9/19 |

OTHER PUBLICATIONS

Yan et al., "A novel intracellular protein delivery platform based on single-protein nanocapsules", Nature Nanotechnology 5: 48-53 (2010) (Year: 2010).*

Yan et al., "Encapsulation of Single Enzyme in Nanogel with Enhanced Biocatalytic Activity and Stability", J Amer Chem Soc 128: 11008-11009 (2006) (Year: 2006).*

Bhuchar, N. et al., "Degradable thermoresponsive nanogels for protein encapsulation and controlled release", Bioconjugate Chemistry, 2011, vol. 23, pp. 75-83.

Goto, Y., et al., "Polymer nanoparticles covered wiht phosphorylcholine groups and immobilized with antibody for high-affinity separation of proteins", Biomacromolecules, 2008, vol. 9, pp. 828-833.

Lewis, A. L., et al., "Crosslinkable coatings from phosphorylcholine-based polymers", Biomaterials, 2001, vol. 22, pp. 99-111.

Lewis, A., et al., "Poly (2-methacryloyloxyethyl phosphorylcholine) for protein conjugation". Bioconjugate Chemistry, 2008, vol. 19, pp. 2144-2155.

Morimoto, N., et al., "Hybrid nanogels with physical and chemical cross-linking structures as nanocarriers", Macromolecular Bioscience, 2005, vol. 5, pp. 710-716.

Ukawa, M., et al., "2-Methacryloyloxyethyl phosphorylcholine polymer (MPC)-coating improves the transfection activity of GALA-modified lipid nanoparticles by assisting the cellular uptake and intracellular dissociation of plasmid NDNA in primary hepatocytes", Biomaterials, 2010, vol. 31, pp. 6355-6362.

PCT International Search Report and Written Opinion dated Mar. 4, 2016, International Application No. PCT/US2015/061838.

Konno et al., "Temporal and spatially controllable cell encapsulation using a water-soluble phospholipid polymer with phenylboronic acid moiety". Biomaterials 28 (2007) 1770-1777.

Lewis et al., "Poly(2-methacryloyloxyethyl phosphorykhoJine) for Protein Conjugation". Bioconjugate Chem. 2008, 19, 2144-2155.

Wang et al., "Encapsulation of Biomacromolecules within Polymersomes by Electroporation". Angew. Chem, Int. Ed. 2012, 51, 11122-11125.

Canton et al., "Fully synthetic polymer vesicles for intracellular delivery of antibodies in live cells". The FASEB Journa/vol. 27, No. 1 , pp. 98-108, Jul. 2017.

* cited by examiner

STEALTH NANOCAPSULES FOR PROTEIN DELIVERY

REFERENCE TO RELATED APPLICATIONS

This application claims priority under Section 119(e) from U.S. Provisional Application Ser. No. 62/084,887, filed Nov. 26, 2014, entitled "STEALTH NANOCAPSULES FOR PROTEIN DELIVERY" by Yunfeng Lu et al., the contents of which are incorporated herein by reference.

TECHNICAL FIELD

The invention relates to protein nanocapsules and in particular, extending the circulating half-life of proteins.

BACKGROUND OF THE INVENTION

Protein therapy, which delivers a therapeutic level of protein that may be absent or insufficient in an individual, is considered the ultimate hope for many incurable diseases. However, the application of peptide drugs and therapeutic proteins is limited by their poor stability and permeability in a physiological environment. Thus, there is a growing effort to circumvent these problems by designing nanostructures that can act as carriers for the delivery of therapeutic proteins.

For the systemic delivery of therapeutic proteins, nanoparticles have long been desired as ideal carriers due to the ease of controlling their structures and properties. Additionally, nanoparticles may be used for the targeted delivery of therapeutic agents to specific pathological sites, allowing for an increase-of-dose effect at the needed sites as well as decreasing any side effects. However, very few nanoformulations have currently been approved for use clinically or in clinical trials. One major obstacle for the in vivo use of nanoparticles is the rapid clearance of nanoparticles by the immune system, which leads to undesired pharmacokinetics and biodistribution. This problem renders most targeting strategies ineffective and reduces the efficacy of both approved nanoformulations and those still in development.

Currently, the main strategy for extending the circulation time of nanoparticles is to coat the particles with polyethylene glycol (PEGylation) to create "stealth" brushes that mimic cell glycocalyx. Indeed, PEGylation has been found to extend the circulation time of particles in vivo. However, up to 25% of patients have been found to exhibit anti-PEG antibodies prior to treatment or develop anti-PEG antibodies after the first administration of PEGylated nanoparticles. Thus, PEGylation of nanoparticles has little prospect of becoming a practical vehicle in the development of nanoparticle-based therapeutics.

SUMMARY OF THE INVENTION

The present invention relates to methods of extending the circulation time and/or lowering the immunogenicity of therapeutic proteins administrated intravenously. In multiple embodiments, the in vivo circulating lifetime of foreign proteins are significantly prolonged by encapsulating them with poly(2-methacryloxyloxyethyl phosphorycholine) (pMPC). By encapsulating the proteins, the protein surfaces are fully covered by a pMPC shell that minimizes adhesion to opsonins and cells, resulting in a dramatic delay in immune recognition and clearance. As further described in the Example section below, biodistribution studies have found that in certain embodiments, over 50% of the injected proteins encapsulated with pMPC (pMPC-Proteins) stay in the bloodstream instead of being trapped in the organs (e.g. over 50% of the injected proteins encapsulated with pMPC stay in the bloodstream for at least 1, 2, 3 or 4 hours). Thus, these methods provide a better alternative to traditional polyethylene glycol (PEG)-based strategies for intravenous delivery of therapeutic agents.

In one aspect of the present invention, a method of extending a circulating half-life of a protein is provided. The method comprises conjugating a protein with an unsaturated vinyl group and encapsulating the protein with a layer of poly(2-methacryloxyloxyethyl phosphorycholine) (pMPC). In one or more embodiments, the layer of pMPC comprises a plurality of 2-methacryloxyloxyethyl phosphorycholine monomers (MPC) polymerized with a N,N'-methylenebisacrylamide (BIS) crosslinker. Typically, the unsaturated vinyl group is a polymerizable acryloyl group. In one embodiment, the layer of pMPC is selected to provide a zwitterionic structure to the encapsulated protein. In one or more embodiments, the layer of pMPC has a thickness of 8 to 11 nm. In other embodiments, the layer of mMPC has a thickness of less than 1, 2, 3, 4 or 5 nm.

In one embodiment, encapsulating the protein with a layer of pMPC extends the half-life of the protein in vivo. In another embodiment, encapsulating the protein with a layer of pMPC delays clearance of the protein by an immune system in vivo. In a further embodiment, encapsulating the protein with a layer of pMPC reduces a probability of the protein binding with opsonins, macrophages or antibodies in vivo. In one instance, the encapsulated protein retains at least 95% of its activity when incubated with trypsin for at least 90 minutes. In another instance, the encapsulated protein retains at least 90% of its activity when incubated in 37° C. for at least 5 days.

In another aspect of the invention, a method of forming a protein nanocapsule is provided. The method comprises conjugating a protein with an unsaturated vinyl group and encapsulating the protein with a layer of poly(2-methacryloxyloxyethyl phosphorycholine) (pMPC). In one or more embodiments, the layer of pMPC is formed by polymerizing a plurality of 2-methacryloxyloxyethyl phosphorycholine monomers (MPC) with a N,N'-methylenebisacrylamide (BIS) crosslinker. Typically, the protein is conjugated with a polymerizable acryloyl group. In one embodiment, the layer of pMPC is selected to provide a zwitterionic structure to the encapsulated protein. In one or more embodiments, the layer of pMPC has a thickness of 8 to 11 nm. In other embodiments, the layer of mMPC has a thickness of less than 1, 2, 3, 4 or 5 nm.

In another aspect of the invention, a composition of matter is provided. The composition of matter comprises a cargo agent and poly(2-methacryloxyloxyethyl phosphorycholine) (pMPC), wherein the pMPC encapsulates the cargo agent. In one or more embodiments, the cargo agent is a protein or polypeptide. In one embodiment, the pMPC comprises a plurality of 2-methacryloxyloxyethyl phosphorycholine monomers (MPC) polymerized with a N,N'-methylenebisacrylamide (BIS) crosslinker. Typically, the cargo agent is conjugated with a polymerizable acryloyl group. In one or more embodiments, the layer of pMPC has a thickness of 8 to 11 nm. In other embodiments, the layer of mMPC has a thickness of less than 1, 2, 3, 4 or 5 nm. In one instance, the encapsulated protein or polypeptide retains at least 95% of its activity when incubated with trypsin for at least 90 minutes. In another instance, the encapsulated protein or polypeptide retains at least 90% of its activity when incubated in 37° C. for at least 5 days.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

Referring now to the drawings in which like reference numbers represent corresponding parts throughout:

FIGS. 2A-F illustrate the structure and the unique properties of pMPC protein nanocapsules, in accordance with one or more embodiments of the invention. FIGS. 2A and 2B depict a transmission electron micrograph showing the uniform size of pMPC-nEGFP (a) and pMPC-nOVA (b). FIG. 2C illustrates the activity comparisons of HRP, GOx, UOx, and AOx between their native forms and their pMPC protein nanocapsules. None of these enzymes shows significant activity loss after encapsulation. FIG. 2D illustrates the thermo-stability of native AOx and pMPC-nAOx when incubating at 37° C. FIG. 2E illustrates the change in activity of native UOx and pMPC-nUOx when challenged with 0.1 mg/mL trypsin at 37° C. FIG. 2F illustrates the amount of proteins adsorbed by the pMPC-nEGFP, pAAm-nEGFP, and native EGFP after the incubation with mouse whole serum. Data represent mean±standard error of the mean (SEM) (2C, 2D, and 2E) and mean±standard derivation (SD) (2F) from three independent experiments.

FIG. 3A illustrates cell viability assays after incubating with native OVA and pMPC-nOVA for 24 hrs. Cell proliferation rates were normalized with those of the untreated cells cultured in the same condition. The viability was assayed with CellTiter Blue. FIG. 3B illustrates the receptor mediated endocytosis (RME) level of native transferrin (Tf) and pMPC-nTf by U87 cells. The RME of Tf is largely inhibited by the encapsulation. FIG. 3C illustrates the cell uptake level of native EGFP and EGFP nanocapsules with different surfaces. FIG. 3D depicts fluorescence images that show the phagocytosis of native OVA (i) but not pMPC-nOVA (iii) after 1 hr incubation with J774A.1 mouse macrophage cells. Opsonization with mouse serum (+MS) enhances the phagocytosis of native OVA (ii) whereas no significant phagocytosis can be observed from pMPC-nOVA after incubation with serum. Cells were stained with Hoechst 33342 for imaging the nuclei. Scalebar: 50 µm. FIG. 3E is a histogram comparing the mean fluorescent intensity accessed from fluorescence-assisted cell sorting (FACS) analysis of the macrophages after incubating with native OVA, native OVA+MS, pMPC-nOVA, and pMPC-nOVA+MS. FIG. 3F illustrates the quantitive analysis of the OVA and pMPC-nOVA uptake by both quiescent and stimulated human peripheral blood mononuclear cells (PBMCs) from 6 donors. FIGS. 3G and 3H illustrate a comparison with the levels of blood IgG, IgE, OVA-specific IgG (OVA-sIgG), and OVA-sIgE of the mice being treated with PBS (blank), native OVA and pMPC-nOVA indicating the OVA becoming less immunogenic after the encapsulation. Data represent mean±SEM from three independent experiments (3A), mean±% Robust coefficient of variation (CV) from FACS data (3E), mean±SD from several independent experiments (n=6 for 3B, 3C; n=5 for 3F, 3G, 3H).

FIG. 4A illustrates single-photon emission computed tomography/X-ray computed tomography (SPECT/CT) images of the animal at different timeS after intravenous administration of radioactive $^{125}$I-pMPC-nEGFP. FIG. 4B illustrates the quantitative analysis of the relative amount of $^{125}$I-pMPC-nEGFP in blood and organs at different time. All the radioactive intensities were normalized with the intensity of heart at 3 hours of each animal. FIG. 4C is a histogram summarizing the relative amount of pMPC-nEGFP distributed in blood and other major organs comparing to the total amount of pMPC-nEGFP at different time after the injection. FIG. 4D illustrates the pharmacokinetics (PK) profiles of native AOx, pAAm-nAOx, and pMPC-nAOx in mice after systemic administration. Data represent mean±SEM from independent experiments (n=3 for 4B and 4C, and n=4 for 4D).

FIGS. 5A-K illustrate the size distribution of various pMPC protein nanocapsules, in accordance with one or more embodiments of the invention.

FIGS. 7A-B illustrate the biodistributions of pMPC-nBSA, in accordance with one or more embodiments of the invention. FIG. 7A illustrates the quantitive analysis of the relative amount of $^{125}$I-pMPC-nBSA in blood and organs at different times. All the radioactive intensities were normalized with the intensity of heart at 3 hours of each animal. FIG. 7B is a histogram summarizing the relative amount of pMPC-nBSA distributed in blood and other major organs comparing to the total amount of pMPC-nBSA at different times after the injection.

DETAILED DESCRIPTION OF THE INVENTION

Many of the techniques and procedures described or referenced herein are well understood and commonly employed using conventional methodology by those skilled in the art. In the description of the preferred embodiment, reference may be made to the accompanying drawings which form a part hereof, and in which is shown by way of illustration a specific embodiment in which the invention may be practiced. It is to be understood that other embodiments may be utilized and structural changes may be made without departing from the scope of the present invention.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

To date, nanoparticle-based therapeutics has shown great potential as a revolutionary delivery strategy that allows for the stabilization of insoluble and fragile proteins. However, applications of nanoparticles are typically limited by a short in vivo circulating time resulting from their clearance by the immune system. Current methods of prolonging circulating time for protein-based therapeutics are mainly achieved by PEGylation, which is described for example in U.S. Pat. No. 4,179,337. However, it has been found that most people tend to develop anti-PEG responses, due in part to the extensive use of PEG in food and cosmetics.

The removal of nanoparticles from the body (i.e. clearance) is mainly achieved by the mononuclear phagocyte system (MPS), also known as the reticuloendothelial system (RES). The macrophages of the MPS can either identify the foreign particles directly, or recognize them via the opsonin proteins bounded to the surface of the foreign particles. Clearly, both pathways are initiated by the binding of nanoparticles with biological contents such as macrophages and opsonins Thus, by minimizing the binding probability, it is possible to delay the MPS clearance of the nanoparticles from the blood, thereby prolonging their circulating lifetime and suppressing their immunogenicity.

In one aspect, the invention disclosed herein provides a rational design of protein and polypeptide nanocapsules that are capable of prolonging the circulating lifetime of any protein or polypeptide in blood. In a further aspect, by using simple wet-chemical approaches, non-fouling protein nanocapsules are provided for a broad range of clinical applications. Generally, this is achieved by encapsulating the protein with a thin layer of poly(2-methacryloxyloxyethyl phosphorycholine) (pMPC) to create a non-fouling surface on top of the protein.

The synthesis strategy of pMPC encapsulated protein nanoparticles (pMPC-nProtein) is achieved by using a modified version of protein encapsulation technology. As illustrated in FIG. 1, in one or more embodiments, the synthesis strategy of pMPC-nProtein is achieved with a two step method. The protein is first conjugated with unsaturated vinyl groups (I), and then wrapped with pMPC polymeric network by co-polymerizing the monomer (2-methacryloxyloxyethyl phosphorycholine, MPC) and the crosslinker (N,N'-Methylenebisacrylamide, BIS) in aqueous solution (II). Due to the adsorption-resistant properties of pMPC, the pMPC coating significantly reduces the probability of the protein binding with opsonins (i), macrophages (ii), or antibodies (iii), thereby delaying clearance by the immune system and extending their circulating half-life. Furthermore, the pMPC coating also prevents the inner protein from directly interacting with proteases, which enhances the stability of the protein during circulation in the bloodstream (thereby extending the time of the protein's circulating half-life in individuals to whom the protein has been administered).

This invention provides advantages such as prolonged blood circulating half-life and lower immunogenicity for most therapeutic proteins. As shown in the Example section below, this invention can significantly increase the circulation time of therapeutic proteins administrated intravenously. The invention also utilizes biocompatible materials that make them harder to be identified by the immune system after being administrated. This protein therapy technology may be applied to various diseases (e.g. gout) and tissue reconstruction and regeneration. Compared to current technology (e.g. traditional PEGylation strategies), the invention provides a more stable structure and the materials used are fully biocompatible and do not trigger immune responses. As a result, the invention allows the therapeutic proteins to have a more favorable pharmacokinetic profile and higher bioavailability.

In one aspect of the present invention, a method of extending a circulating half-life of a protein is provided. The method comprises conjugating a protein with an unsaturated vinyl group and encapsulating the protein with a layer of poly(2-methacryloxyloxyethyl phosphorycholine) (pMPC). In one or more embodiments, the layer of pMPC comprises a plurality of 2-methacryloxyloxyethyl phosphorycholine monomers (MPC) polymerized with a N,N'-methylenebisacrylamide (BIS) crosslinker. Typically, the unsaturated vinyl group is a polymerizable acryloyl group. In one embodiment, the layer of pMPC is selected to provide a zwitterionic structure to the encapsulated protein. In one or more embodiments, the layer of pMPC has a thickness of 8 to 11 nm. In other embodiments, the layer of mMPC has a thickness of less than 1, 2, 3, 4 or 5 nm.

In one embodiment, encapsulating the protein with a layer of pMPC extends the half-life of the protein in vivo. In another embodiment, encapsulating the protein with a layer of pMPC delays clearance of the protein by an immune system in vivo. In a further embodiment, encapsulating the protein with a layer of pMPC reduces a probability of the protein binding with opsonins, macrophages or antibodies in vivo. In one instance, the encapsulated protein retains at least 95% of its activity when incubated with trypsin for at least 90 minutes. In another instance, the encapsulated protein retains at least 90% of its activity when incubated in 37° C. for at least 5 days.

In another aspect of the invention, a method of forming a protein nanocapsule is provided. The method comprises conjugating a protein with an unsaturated vinyl group and encapsulating the protein with a layer of poly(2-methacryloxyloxyethyl phosphorycholine) (pMPC). In one or more embodiments, the layer of pMPC is formed by polymerizing a plurality of 2-methacryloxyloxyethyl phosphorycholine monomers (MPC) with a N,N'-methylenebisacrylamide (BIS) crosslinker. Typically, the protein is conjugated with a polymerizable acryloyl group. In one embodiment, the layer of pMPC is selected to provide a zwitterionic structure to the encapsulated protein. In one or more embodiments, the layer of pMPC has a thickness of 8 to 11 nm. In other embodiments, the layer of mMPC has a thickness of less than 1, 2, 3, 4 or 5 nm.

In another aspect of the invention, a composition of matter is provided. The composition of matter comprises a cargo agent and poly(2-methacryloxyloxyethyl phosphorycholine) (pMPC), wherein the pMPC encapsulates the cargo agent. In one or more embodiments, the cargo agent is a protein or polypeptide. In one embodiment, the pMPC comprises a plurality of 2-methacryloxyloxyethyl phosphorycholine monomers (MPC) polymerized with a N,N'-methylenebisacrylamide (BIS) crosslinker. Typically, the cargo agent is conjugated with a polymerizable acryloyl group. In one or more embodiments, the layer of pMPC has a thickness of 8 to 11 nm. In other embodiments, the layer of mMPC has a thickness of less than 1, 2, 3, 4 or 5 nm. In one instance, the encapsulated protein or polypeptide retains at least 95% of its activity when incubated with trypsin for at least 90 minutes. In another instance, the encapsulated protein or polypeptide retains at least 90% of its activity when incubated in 37° C. for at least 5 days.

EXAMPLES

Example 1: Encapsulation with the pMPC Shell does not Compromise the Protein Structure The successful preparation of pMPC protein nanocapsules was demonstrated using enhanced green fluorescence protein (EGFP) and ovalbumin (OVA). After encapsulation with pMPC, the protein nanocapsules showed a uniform, spherical morphology with an average diameter of 25±5 nm according to transmission electron microscope (TEM) images of pMPC-nEGFP (FIG. 2A) and pMPC-nOVA (FIG. 2B). Considering that the particle size of EGFP and OVA is around 8 nm, the average thickness of the pMPC shell is around 8-11 nm. Because the pMPC coating is formed using a very mild reaction in aqueous media, the proteins encapsulated inside are able to retain their structures and biological functions.

To verify this, four enzymes, including horseradish peroxidase (HRP), glucose oxidase (GOx), uricase (UOx), and alcohol oxidase (AOx), were encapsulated with the same method, and their enzymatic activities were compared with their native counterparts, respectively. FIG. 2C shows the relative catalytic efficiency of the pMPC-nProteins in comparison to their native forms. Based on the results, there was no significant difference in the overall catalytic efficiency before and after encapsulation, although all the pMPC-encapsulated enzymes showed a slightly lower activity compared to their native versions. This activity loss may be attributed to the 8 nm-thick pMPC coating that decreases diffusivity when the substrates are transferred across the pMPC shell to bind with the enzyme inside, which leads to an increase of the apparent Michaelis constant (KM) (Table 1). Both the increase of KM and no significant loss in enzymatic activity suggest that the encapsulation does not compromise the protein structure. This further indicates that the pMPC-encapsulation method is generally applicable to most proteins and enzymes without compromising their biological functions.

TABLE 1

Kinetic parameters of pMPC-nHRP, pMPC-nGOx, pMPC-nUOx, pMPC-nAOx and their native counterparts

| Sample | $K_M^{app}$(mM) | $k_{cat}^{app}$ (s$^{-1}$) | $K_{cat}^{app}/K_M^{app}$ mM$^{-1}$ s$^{-1}$ | % |
|---|---|---|---|---|
| native HRP | 0.0925 ± 0.0213 | 4.03 × 10$^2$ | 4356.7 ± 989.0 | 100 ± 22.7 |
| pMPC-nHRP | 0.121 ± 0.0340 | 4.80 × 10$^2$ | 3966.9 ± 1114.7 | 91.1 ± 28.1 |
| native GOx | 18.00 ± 6.21 | 87.9 | 4.883 ± 1.684 | 100 ± 34.5 |
| pMPC-nGOx | 21.56 ± 6.70 | 77.6 | 3.600 ± 1.119 | 73.7 ± 31.1 |
| native UOx | 0.0219 ± 0.0017 | 3.36 | 153.4 ± 11.8 | 100 ± 7.7 |
| pMPC-nUOx | 0.0259 ± 0.0043 | 3.59 | 138.6 ± 22.9 | 90.4 ± 16.5 |
| native AOx | 3.109 ± 0.720 | 18.8 | 6.047 ± 1.428 | 100 ± 23.61 |
| pMPC-nAOx | 5.120 ± 1.433 | 23.4 | 4.570 ± 1.279 | 75.6 ± 28.00 |

Example 2: Encapsulation with the pMPC Shell Enhances Protein Stability

As illustrated in the scheme, the pMPC shell wrapped outside the protein is synthesized from the MPC monomer directly. Unlike traditional self-assembly and "graft-on" methods for coating the protein, this polymerization method prepares a cross-linked and dense polymeric network that ensures a full coverage of the inner protein during circulation in the blood, where the shearing force is high and the physiological condition is changing continuously. As a result, the nanocapsule disclosed herein provides a stable microenvironment for the protein inside, which effectively enhances its stability.

To verify this, the stability of protein nanocapsules was first challenged against thermal denaturation. Using AOx as a model protein, native AOx and pMPC-nAOx were incubated under 37° C. for 5 days and their enzymatic activities were monitored at different times. According to the activity comparison (FIG. 2D), native AOx lost more than 60% of its activity, suggesting that its structure was compromised during the incubation. However, pMPC-nAOx retained 90% of its activity, indicating that the encapsulation had indeed enhanced protein stability.

Example 3: Encapsulation with the pMPC Shell Prevents Proteolysis and Lowers Protein Adsorption The pMPC shell further isolates the encapsulated protein from the outer environment. During circulation, proteins, cells, tissues and organs have to interact with the pMPC shell instead of the surface of the inner protein, which provides two major benefits for prolonging the circulating lifetime of the protein on a molecular level. First, the pMPC shell prevents the protein from proteolysis by inhibiting the binding of proteases. Exemplified with UOx (FIG. 2E), native UOx lost its activity completely within 40 min when incubating with trypsin, whereas the pMPC-nUOx retained more than 95% of its activity even after 90 min incubation. Second, the pMPC shell replaces the protein surface with a zwitterionic structure, resulting in low protein adsorption onto the pMPC protein nanocapsules. FIG. 2F compares the amount of protein adsorbed by different EGFP samples after 30 min incubation with mouse serum (MS) at 37° C. Clearly, the native EGFP adsorbed a large amount of serum proteins, whereas the pMPC-nEGFP showed no significant protein adsorption compared to the control. As expected, encapsulation with a non-zwitterionic polymer (pAAm-nEGFP) also resulted in the significant adsorption of serum protein, confirming that the pMPC shell plays a critical role in lowering protein adsorption. Considering that protein adsorption usually leads to opsonization and agglomeration that accelerates MPS clearance, the pMPC coating should remarkably delay the identification of the encapsulated protein by macrophages, thereby extending the circulation half-life of the encapsulated protein in the body.

Example 4: Encapsulation with the pMPC Shell Improves Biocompatibility

Figure 1:
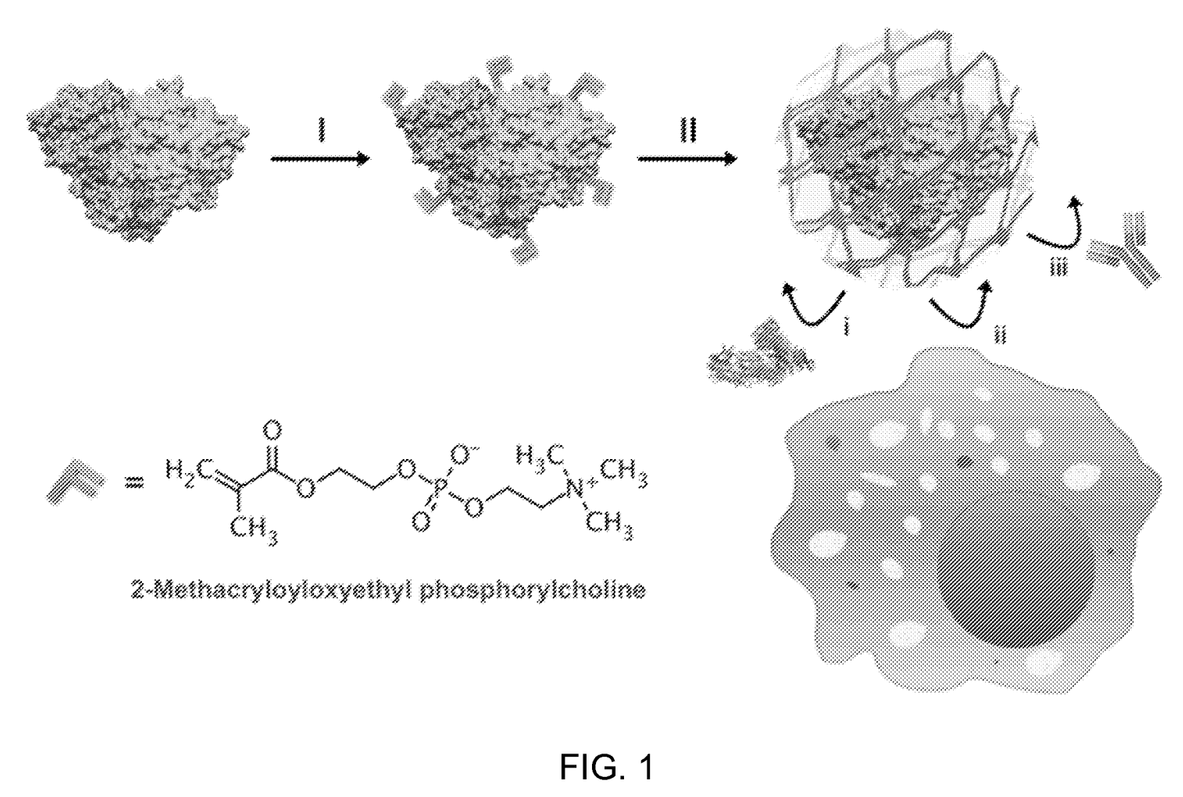
FIG. 1 is a schematic illustration of the synthesis of a pMPC protein nanocapsule (pMPC-nProtein), in accordance with one or more embodiments of the invention. The encapsulation of the protein with pMPC is achieved by two steps. The protein is anchored with polymerizable acryloyl groups on the surface by a conjugating reaction (I); subsequentially, the protein is wrapped with pMPC polymeric network through in situ polymerization of 2-methacryloxyloxyethyl phosphorycholine (II). The resulting protein nanocapsule is fully covered by a pMPC shell, which is non-fouling to opsonin proteins (i), various types of cells including macrophages (ii), and antibodies (iii).
Figure 3A:
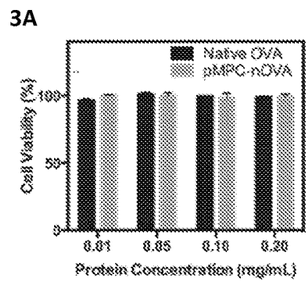
FIGS. 3A-H illustrate the reduced cell-uptake and phagocytosis of proteins by pMPC-encapsulation, in accordance with one or more embodiments of the invention.
Figure 3B:
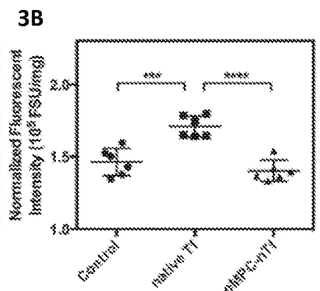

The pMPC shell also affords the protein nanocapsules with better biocompatibility, which is important for a delivery strategy to assure successful delivery with minimal side effects. Since pMPC is a non-toxic and biocompatible material, encapsulation with pMPC does not bring additional toxicity. This was confirmed in illustrative experiments that showed a negligible difference in cell viability after exposure to native proteins and pMPC-nProteins for 24 hours respectively (see, e.g. FIG. 3A). Furthermore, pMPC encapsulation prevents the protein from directly interacting with cell surfaces, which significantly delays their internalization into the cells. For example, transferrin (TO is a protein that is capable of internalizing into U87 cells via receptor-mediated endocytosis (RME). However, pMPC encapsulation blocks the binding between Tf and Tf receptors (TfR), leading to the inhibition of RME which thereby reduces the amount of Tf internalization into the U87 cells (FIG. 3B).

Figure 3C:
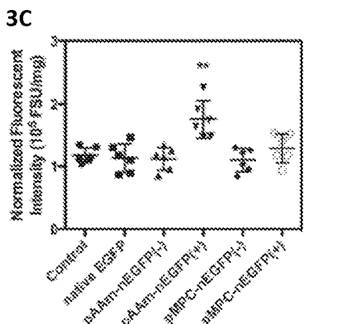

Further investigation on the interactions between pMPC protein nanocapsules and cell surfaces was achieved by incubating U87 cells with an equal amount of native EGFP and EGFP nanocapsules with different surface materials and zeta potentials, respectively. FIG. 3C compares the amount of EGFP internalized into the cells after the incubation. According to the results, nanocapsules with a negatively charged surface (pAAm-nEGFP(−) and pMPC-nEGFP(−)) were not favorable for cell uptake, which agrees with what has been reported in literature. For the positive ones, pAAm-nEGFP(+) showed a high level of cell uptake, whereas pMPC-nEGFP(+) showed a very low level uptake that is not significant compared to that of the control (no EGFP) and native EGFP, despite a similar amount of positive charge possessed on both positively charged nanocapsules (pAAm-nEGFP(+), $\zeta$=+1.27 mV; pMPC-nEGFP(+), $\zeta$=+1.08 mV). Obviously, the pMPC shell delayed the cellular uptake, which may be attributed to its non-fouling feature that prevents the nanocapsules from binding with the cell membrane. Without stable binding, it is impossible for the cell to stabilize the high curvature of the membrane, which is essential for the formation of endosomes.

Example 5: Encapsulation with the pMPC Shell Delays Phagocytosis

Based on the fact that the pMPC shell can delay cellular uptake as well as inhibit opsonization, it is contemplated that pMPC-encapsulation may also be used to delay the phagocytosis of macrophages, regardless of the presence of opsonins. To verify this, J744A.1 mouse macrophage cells, rhodamine B (RhB)-labeled native OVA, and RhB-labeled pMPC-nOVA were employed to evaluate the level of phagocytosis. Both native OVA and pMPC-nOVA were incubated with PBS (−MS) and mouse serum (+MS) prior to the exposure to the macrophages, respectively.

Figure 3D:
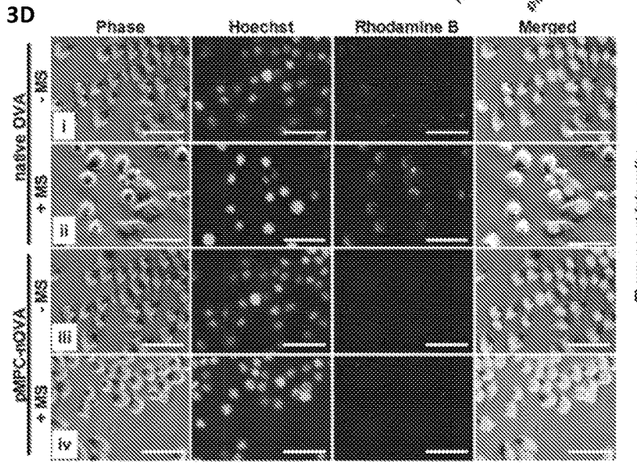
Figure 3E:
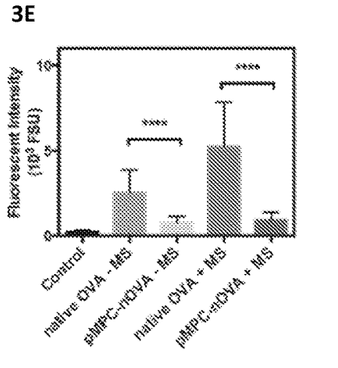

As expected, these samples resulted in great differences in phagocytosis levels after 1 hour of incubation with the macrophages. According to the microscope images (FIG. 3D), both native OVA samples showed obvious rhodamine B fluorescent signals (FIG. 3D, i & ii), indicating a high level of phagocytosis. In contrast, a very low level of phagocytosis was observed in the pMPC-nOVA samples (FIG. 3D, iii & iv). A significant enhancement in phagocytosis from native OVA samples was also observed after incubating with mouse serum, suggesting that the opsonization of native OVA accelerated the phagocytosis. However, no obvious differences in phagocytosis levels were observed in pMPC-nOVA samples after serum incubation, because the non-fouling ability of the pMPC shell prevented the nanocapsules from opsonization, which was also confirmed by its low protein adsorption (FIG. 2F). Fluorescence-activated cell sorting (FACS) analysis indicated an up to 6-fold decrease in mean fluorescent intensity of the macrophages treated with pMPC-nOVA+MS/−MS (FIG. 3E, & Table 2) compared to those treated with native OVA+MS/−MS respectively. This also confirms the effectiveness of pMPC-encapsulation in the inhibition of opsonization and the delay of phagocytosis. Since phagocytosis is critical to the MPS clearance of the nanocapsules, it is possible to extend the circulation half-life of proteins by pMPC-encapsulation.

TABLE 2

Summary of the FACS results

| Sample | Events | % Gated | % RhB− | % RhB+ | Mean Fluorescence | % Robust CV |
|---|---|---|---|---|---|---|
| Control | 10000 | 43.5 | 99.8 | 0.207 | 217 | 54.9 |
| native OVA | 10000 | 20.3 | 5.03 | 95 | 2558 | 51.3 |
| native OVA + MS | 10000 | 44.1 | 0.159 | 99.8 | 5229 | 49.8 |
| pMPC-nOVA | 10000 | 38.9 | 63.7 | 36.3 | 810 | 45.4 |
| pMPC-nOVA + MS | 14508 | 29.1 | 48.2 | 51.8 | 946 | 48.5 |

Example 6: Encapsulation with the pMPC Shell Decreases Immunogenicity

In addition to MPC clearance, foreign proteins and their nanoformulations can also be effectively eliminated by the adaptive immune system, which can identify and neutralize the foreign substances by generating corresponding antibodies. Moreover, adaptive immunity usually generates memory B cells that can identify the antigens directly and produce antibodies quickly, resulting in accelerated blood clearance (ABC) of the foreign substances. To date, most intravenous nanoformulations suffer from the ABC phenomenon, including the widely used PEGylation nanostructures.

However, adaptive immune system activation and the generation of memory B cells require an essential step called antigen presentation when introducing the foreign substances for the first time. Antigen presentation is initiated by the identifying, engulfing, and digesting of antigens by antigen presenting cells (APCs). Thus, nanoformulations that inhibit the uptake by APCs are able to avoid immune activation, resulting in a decrease in immunogenicity, minimal occurrence of the ABC phenomenon, and therefore a significant extension in blood circulating lifetime.

Figure 3F:
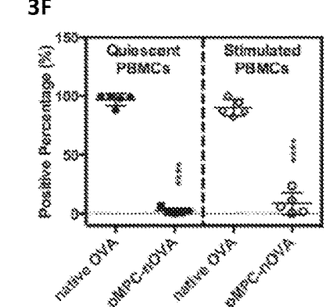
Figure 3G:
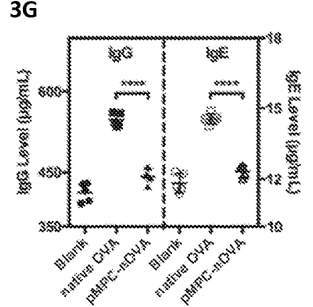
Figure 3H:
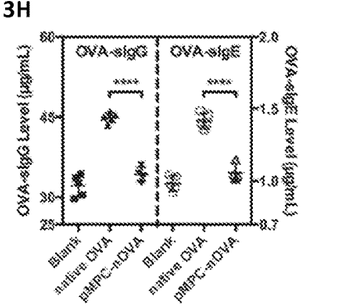

To evaluate the engulfment of pMPC-nProteins, both quiescent and stimulated human peripheral blood mononuclear cells (PBMCs) from 6 donors were employed and incubated with RhB-labeled native OVA and RhB-labeled pMPC-nOVA, respectively. FIG. 3F summarizes the results, indicating that pMPC-encapsulation can effectively hinder the engulfment of OVA by PBMCs even after the stimulation. Considering that the PBMCs consist of most major types of APCs, it is predicted that the pMPC-nProteins will present minimal immunogenicity, which was then accessed by measuring the antibody levels (IgG and IgE) after the in vivo administration of pMPC-nOVA and native OVA in mice. FIG. 3G compares the IgG and IgE levels of the mice (BALB/C) treated with PBS (control), native OVA, and pMPC-nOVA. Due to the strong immunogenicity of OVA, the mice treated with native OVA expressed high levels of IgG and IgE after injection. However, no significant elevation in IgG and IgE levels were observed in the pMPC-nOVA-treated group, suggesting that the pMPC-encapsulation indeed suppressed immune activation. Similar results (FIG. 3H) were also observed in the OVA-specific IgG and IgE levels (OVA-sIgG and OVA-sIgE), indicating that the pMPC shell wrapping outside the OVA blocked its presentation by APCs. By minimizing the phagocytosis and the engulfment of macrophages and APCs, pMPC-nProteins have successfully avoided being identified and neutralized by major clearance pathways, including MPS clearance and adaptive immunity. Therefore, it is possible for pMPC-nProteins to show a prolonged blood circulating half-life, and an ideal biodistribution after intravenous administration.

Figure 4A:
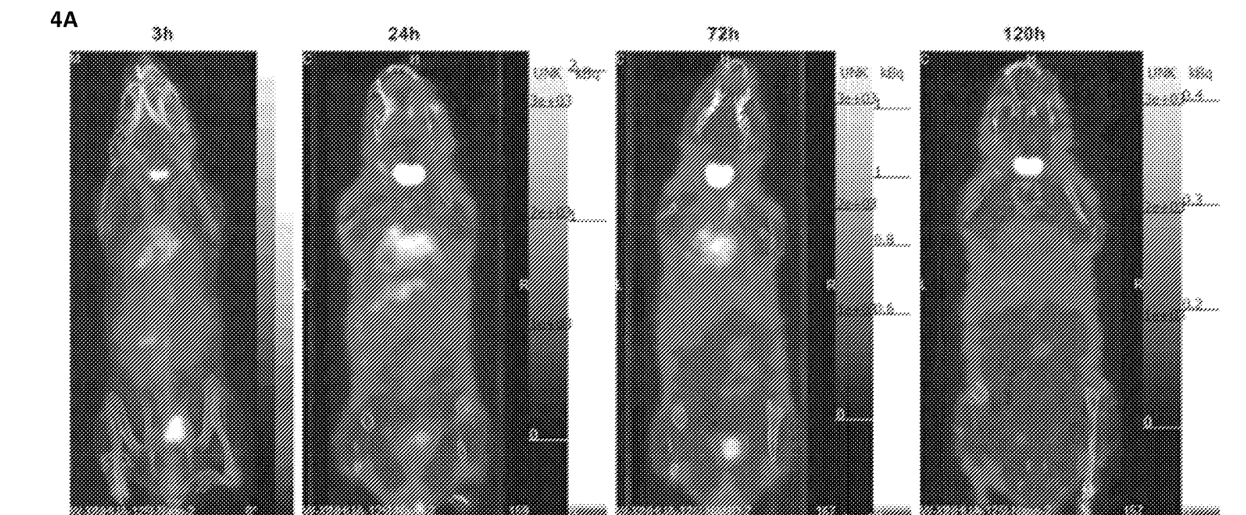
FIGS. 4A-D illustrate the long-circulation and low immunogenicity of pMPC protein nanocapsules in vivo, in accordance with one or more embodiments of the invention.
Figure 4B:
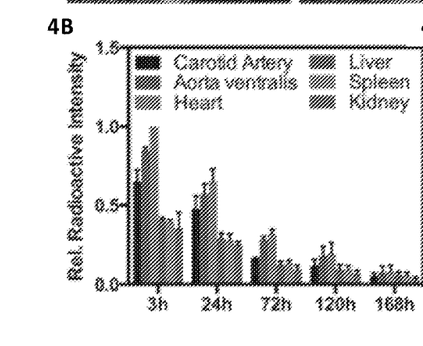
Figure 4C:
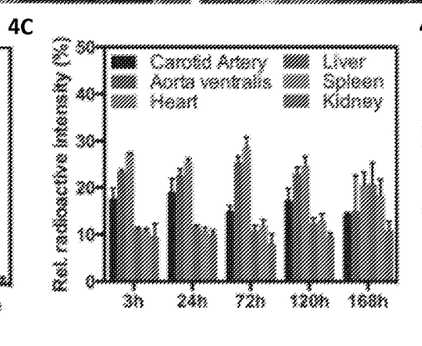

Example 7: Evaluation of the In Vivo Circulating Ability of Proteins Encapsulated with pMPC To evaluate the in vivo circulating ability of pMPC-nProteins, pMPC-nEGFP was labeled with radioactive 125I and the nanocapsules were injected into mice (Chinese Kun Ming Mouse) via their tail vein. The distribution and circulation of pMPC-nEGFP were traced with single-photon emission computed tomography (SPECT). The SPECT/X-ray computed tomography (CT) images collected within 7 days are shown in FIG. 4A. From the images (FIG. 4A) and the histogram (FIG. 4B), a significant portion of pMPC-nEGFP circulating in the blood stream at 72 hours post-injection was clearly observed. For a better understanding of the circulating behavior of pMPC-nEGFP, the radioactive intensity at different tissues and organs was normalized with their corresponding total radioactive intensity to get the biodistribution of pMPC-nEGFP at different times (FIG. 4C). Clearly, the distributions of pMPC-nEGFP in the blood and organs were nearly identical at different times, and the amount of pMPC-nEGFP in the blood was significantly higher than those detected in the liver, spleen, and kidney. This is a very unique biodistribution among all current nanoparticle-based delivery strategies, which typically loses 90% of the nanoformulations through accumulation in the organs shortly after administration.

A major difference from current nanoparticle-based vehicles is that the pMPC-nProtein has a very dense, stable, and non-fouling pMPC shell that encapsulates the inner protein completely at any moment. As discussed previously, this pMPC shell is capable of delaying phagocytosis by macrophages, which are primarily located in the liver, kidney, spleen, lung, lymph nodes, and central nervous system. The delay of phagocytosis decreases the probability of the protein nanocapsules from being captured, thereby reducing their accumulation in the organs and extending their circulating half-life in the blood. Similar results were also achieved with pMPC-nBSA (FIGS. 7A-B), confirming that the unique circulating and distributing behaviors were attributed to the pMPC shell instead of the encapsulated proteins.

Figure 4D:
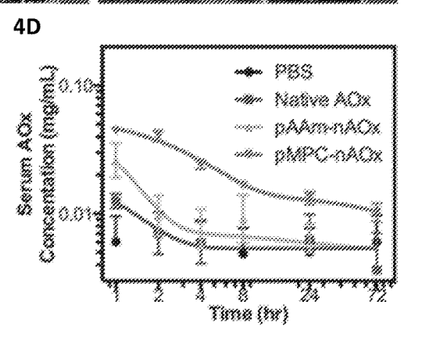
Figure 5A:
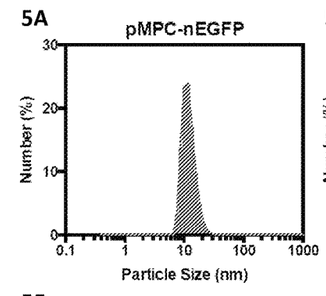
FIG. 5A illustrates pMPC-nEGFP (mean diameter: 12.16 nm)
Figure 5B:
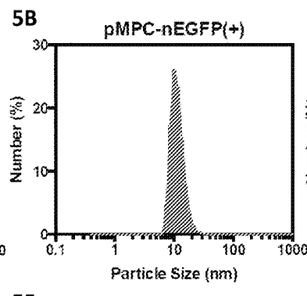
FIG. 5B illustrates pMPC-nEGFP(+) (mean diameter: 11.62 nm)
Figure 5C:
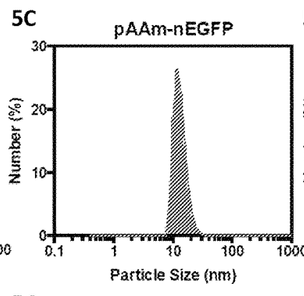
FIG. 5C illustrates pAAm-nEGFP (mean diameter: 13.25 nm)
Figure 5D:
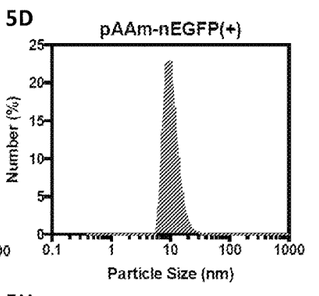
FIG. 5D illustrates pAAm-nEGFP(+) (mean diameter: 10.82 nm)
Figure 5E:
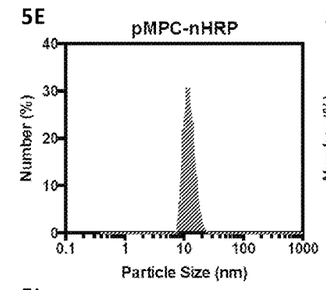
FIG. 5E illustrates pMPC-nHRP (mean diameter: 12.46 nm)
Figure 5F:
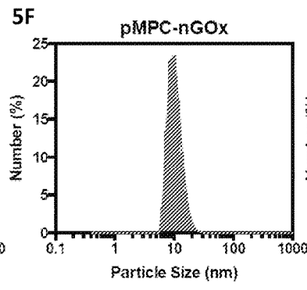
FIG. 5F illustrates pMPC-nGOx (mean diameter: 10.61 nm)
Figure 5G:
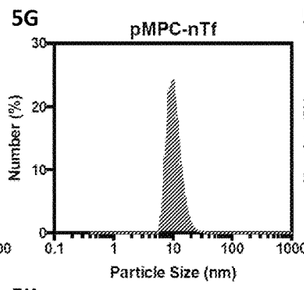
FIG. 5G illustrates pMPC-nTf (mean diameter: 10.78 nm)
Figure 5H:
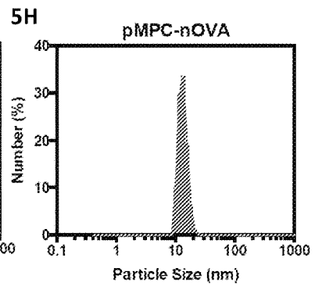
FIG. 5H illustrates pMPC-nOVA (mean diameter: 13.46 nm)
Figure 5I:
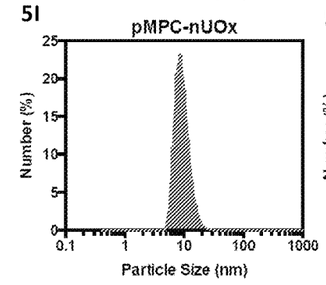
FIG. 5I illustrates pMPC-nUOx (mean diameter: 9.556 nm)
Figure 5J:
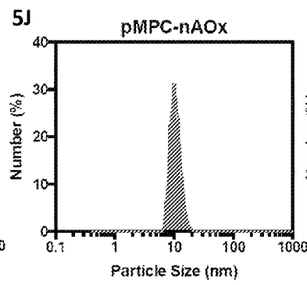
FIG. 5J illustrates pMPC-nAOx (mean diameter: 10.68 nm)
Figure 5K:
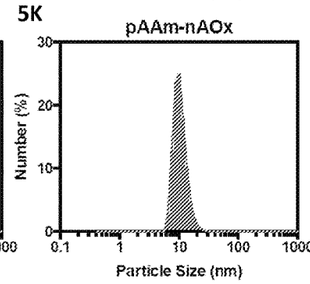
FIG. 5K illustrates pAAm-nAOx (mean diameter: 10.54 nm).
Figure 6A:
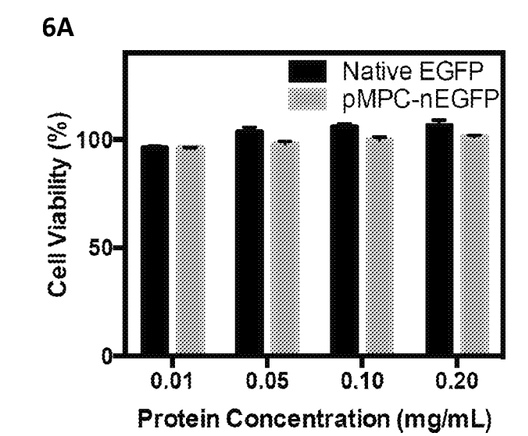
FIGS. 6A-D illustrate the viability of the cells treated with pMPC-nEGFP, pMPC-nOVA, pMPC-nUOx, and pMPC-nAOx and their corresponding native proteins, in accordance with one or more embodiments of the invention.
Figure 6B:
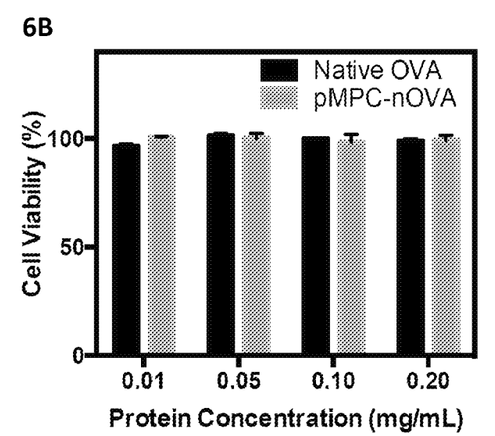
Figure 6C:
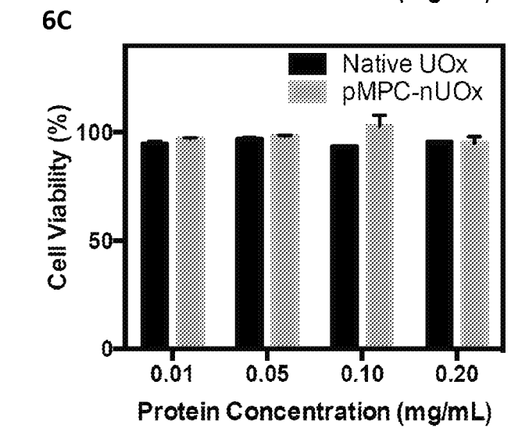
Figure 6D:
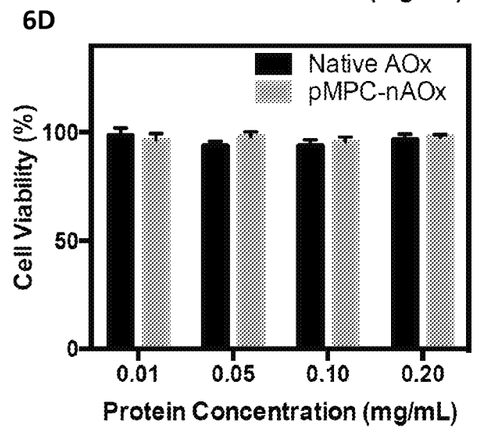

To further verify this, pMPC-nAOx was injected into mice (C57BL/6) and its pharmacokinetics (PK) was determined by measuring the AOx activity in the blood within 72 hours post-injection. As a comparison, the PK of native AOx and pAAm-nAOx were also measured in parallel. FIG. 4D summarizes the results, indicating a much higher serum AOx concentration in pMPC-nAOx treated mice compared to those treated with native AOx and pAAm-nAOx. Data analysis with a two-compartment model (Table 3) reveals that the elimination half-lives of pMPC-nAOx (t1/2, αphase=2.134 h, t1/2, β phase=88.11 h) are 6-fold higher compared to those of native AOx (t1/2, α phase=0.6074 h, t1/2, β phase=0.6087 h) and pAAm-nAOx (t1/2, α phase=0.4297 h, t1/2, β phase=13.83 h), confirming the long-circulating capability of pMPC-nProtein, which is consistent with the SPECT/CT results. Moreover, the PK study also confirms that the pMPC shell can retain the biological activity of the protein encapsulated, which is essential for the delivery of therapeutic proteins.

TABLE 3

Pharmacokinetics parameters of native AOx and nanocapsules

| Parameters | native AOx | PAAm-nAOx | PMPC-nAOx |
|---|---|---|---|
| $k_{\alpha\ phase}$ (h$^{-1}$) | 1.141 | 1.613 | 0.3248 |
| $t_{1/2,\ \alpha\ phase}$ (h) | 0.6074 | 0.4297 | 2.134 |
| $\tau_{\alpha\ phase}$ (h) | 0.8763 | 0.6199 | 3.079 |
| $k_{\beta\ phase}$ (h$^{-1}$) | 1.139 | 0.05013 | 0.007867 |
| $t_{1/2,\ \beta\ phase}$ (h) | 0.6087 | 13.83 | 88.11 |
| $\tau_{\beta\ phase}$ (h) | 0.8782 | 19.95 | 127.1 |

To conclude, a general and practical strategy for extending the circulating half-life of therapeutic proteins by encapsulating them with pMPC has been demonstrated. With this strategy, proteins can be encapsulated with a dense, stable, and non-fouling pMPC shell that is superior to the current stealth strategies in extending circulating half-life and suppressing immunogenicity. Considering that a large number of therapeutic proteins and enzymes are kept from clinical use due to their low bioavailability and strong immunogenicity, the pMPC-encapsulation method provides a straightforward solution that could accelerate their development as clinical therapeutics for many diseases. Moreover, since long-circulation has been proven as a crucial property of nano-carriers to achieve the accumulation of therapeutic agents in specific tissues and organs, the pMPC-encapsulation method provided herein can help address this fundamental problem in the design of advanced targeted delivery strategies.

Example 8: Methods

Quantification of the Protein Adsorption

The protein adsorption amount of different samples was determined with the following method. EGFP was encapsulated with pMPC and polyacrylamide (pAAm) according to the methods described above and previous report, respectively. 10 μL of PBS (control), pMPC-nEGFP (1 mg/mL), pAAm-nEGFP (1 mg/mL), and native EGFP (1 mg/mL) were mixed with 30 µL of mouse whole serum and incubated at 37° C. for 30 min. After incubation, samples were filtered and washed with PBS for 3 times with centrifugal filtration (molecular weight cut-off, MWCO=100 kDa) to remove the unabsorbed serum proteins. After reconstituting with 50 µL of PBS, the EGFP amount in every sample was determined by measuring their absorbance at the wavelength of 450 nm with a nanodrop. For the better quantification of the amount of adsorbed proteins, specific amounts of native EGFP were added to the samples respectively to ensure the same EGFP concentrations among all the samples. Finally, the amount of protein adsorbed was determined by measuring the overall protein concentration of each sample with BCA assay using BSA as the standard. Statistical analyses were performed using the Tukey post-test following a one-way ANOVA. $P<0.05$ or less was considered significant.

Cell-Uptake and Phagocytosis Studies

The study on receptor mediated endocytosis (RME) of Tf was achieved by incubating fluorescence-labeled native Tf and pMPC-nTf with U87 cells, and then evaluated the uptake by measuring the cellular fluorescence intensity. Briefly, U87 cells were plated in a 96-well plate at 5 k cells/well one day prior to the exposure to the native Tf and pMPC-nTf. After incubation at 37° C. for 4 hours, cells were rinsed with PBS (1×) for three times to remove the excess samples and culture medium. Fluorescence intensity of the cells were read out using a plate reader (Fujifilm BAS-5000). After the measurement of the fluorescence, the cells were lysed with cell lysis buffer, and the total protein concentration of each well of cells was determined with BCA assay using BSA as standard. The fluorescence intensity of each well was then normalized with the corresponding protein concentration. The cell-uptake of EGFP with different surfaces was achieved with the similar method, which is detailed in the supplementary information. All the statistical analyses were performed using the Tukey post-test following a one-way ANOVA. $P<0.05$ or less was considered significant.

The phagocytosis was studied using J774A.1 mouse macrophages as model cells and rhodamine B (RhB)-labeled native OVA/pMPC-nOVA as model protein. Macrophage cells were cultured according to the standard protocol (DMEM with 10% FBS, 37° C., 5% carbon dioxide), and were plated into a 96-well plate (5 k cells/well) 24 hours prior to the phagocytosis studies. Since the J774A.1 cells have complement receptor (C3R) expressed, complement activation, which is a major type of opsonization, was also tested by incubating the native OVA and pMPC-nOVA with mouse whole serum at 37° C. for 30 min respectively (native OVA+MS and pMPC-nOVA+MS) before exposure to the macrophage cells. Native OVA, native OVA+MS, pMPC-nOVA and pMPC-nOVA+MS were then added to the cell cultures respectively, and incubated for 1 hour. For better imaging, Hoechst 33342 was added to each well of cells and further incubating for 20 min to stain the nuclei. After incubation, cells were rinsed with PBS (1×) for three times and were observed using a fluorescence microscope (Carl Zeiss Axio Observer). For the better quantification of the phagocytosis, we also cultured J774A.1 cells in a 24-well plate at the density of 30 k cells/well, and then exposed them to the four OVA-based samples described above. After detaching the cells by scraping, the phagocytosis levels were accessed with flow cytometry analysis (BD LSRFortessa cell analyzer). All flow cytometry data were analyzed using FlowJo.

Pharmacokinetics Studies and Data Analysis

Pharmacokinetics (PK) profiles of native AOx, pAAm-nAOx, and pMPC-nAOx were accessed by monitoring the residual AOx activity in plasma after intravenous administration. Briefly, 12 mice (C57BL/6) were divided into 3 groups and injected with 100 µg of native AOx, pAAm-nAOx, and pMPC-nAOx (1 mg/mL) via the tail vein, respectively. As a negative control, another 3 mice were injected with 100 µL of PBS. The blood samples (20 µL) were then taken from the tails at 1 h, 2 h, 4 h, 8 h, 24 h, and 72 h after the injection. The blood samples were then centrifuged at 20 krpm for 5 min to remove the blood cells, and the AOx activity in the plasma was measured using an AOx enzyme activity assay. Detailed experiment procedure and AOx activity measurement are provided in the supplementary information. The analysis of the PK data was achieved by fitting the data using a two-phase exponential decay model with the constraints of Y0<0.1 (maximum AOx concentration cannot be higher than 0.1 mg/mL) and Plateau=0.005354 (the mean background value from the negative control).

Fluorescence-Labeling of Ovalbumin (OVA) and Transferrin (Tf)

For the imaging purposes, two of the proteins, OVA and Tf, were fluorescene-labeled with rhodamine B (RhB) and fluorescence (FITC), respectively. The fluorescence-labeling of these proteins were achieved using the conjugation method. Briefly, proteins was first dissolved with water and dialyzed against sodium carbonate buffer (20 mM, pH 8.5) to remove any ammonium sulfate that usually exists in the stock protein powder. After dialysis, the proteins were diluted to 5 mg/ml with sodium carbonate buffer (20 mM, pH 8.5). Rhodamine B isothiocyanate (RhB-TIC) and fluorescence isothiocyanate (FITC) were dissolved with DMSO to make 1% (w/v) stock solutions, respectively. Then the RhB-TIC and FITC stock solutions were added into OVA and Tf solutions at the molar ratio of 5:1 (Dye:Protein), respectively. The reactions were kept at 4° C. overnight, and then dialyzed against sodium carbonate buffer (20 mM, pH 8.5) to remove the unconjugated dye.

Acryloxylation of Proteins

To enable the incorporation of protein into the pMPC polymeric nanocapsule, proteins were first conjugated with N-acryloxysuccinimide (NAS) to attach acryloyl groups onto their surfaces. A typical procedure for the conjugation is described as follow. Protein (~10 mg/mL) was first dialyzed against sodium carbonate buffer (20 mM, pH 8.5) to remove any ammonium sulfate that usually exists in the stock protein powder. After dialysis, protein solution was diluted to 5 mg/mL with sodium carbonate buffer (20 mM, pH 8.5), followed by adding NAS solution (10% in DMSO, m/v) to perform the conjugation. The amount of NAS used is at 20:1 molar ratio (NAS to protein), and the conjugation is achieved by keeping the reaction at 4° C. for 1 h. The solution was then thoroughly dialyzed against pH 7.0 phosphate buffer (20 mM) with a dialysis tubing membrane (MWCO=10 kDa, Sigma-Aldrich) to remove any unreacted NAS. Acryloylated enzyme solutions were store at 4° C. for further uses.

The average number of acryloyl groups conjugated onto the proteins was determined by measuring the residual (unreacted) lysine on the protein molecule with a fluoresamine assay. Briefly, fluoresamine was first dissolved in anhydrous DMSO to make a 3 mg/mL stock solution. Native protein and its acryloylated counterpart were prepared as 1 mg/mL solutions with 0.1 M phosphate buffer (pH=7.0), respectively. The native and the acryloylated proteins were then diluted with 0.1 M phosphate buffer (pH=7) to make a series of solutions with concentrations 0.00781, 0.01563, 0.03125, 0.0625, 0.125, 0.25, 0.5, and 1 mg/mL; pipette 100 µL of each solution to an opaque 96-well plate, respectively. 30 µL of the fluoresamine solution was then added into each well; the plate was then incubated for 1 h at room temperature (25° C.). After the incubation, fluorescence intensity (Ex=360 nm, Em=465 nm) was read with a plate reader. The number of residual lysine was then estimated by comparing the fluorescent intensity of the acryloylated and the native enzymes. The number of acryloyl groups conjugated onto the proteins is listed in Table 4.

TABLE 4

Average number of acryloyl groups conjugated to the proteins

| Protein | Total No. of Lys | Unreated Lys (%) | Average No. of acryloyl groups conjugated |
|---|---|---|---|
| EGFP | 20 | 42.24% | 11.55 |
| OVA | 20 | 22.27% | 15.55 |
| HRP | 5 | 13.71% | 4.32 |
| GOx | 15 | 44.47% | 8.33 |
| UOx | 26 | 34.69% | 16.98 |
| AOx | 38 | 53.15% | 17.80 |
| Tf | 58 | 68.27% | 18.40 |
| BSA | 59 | 71.64% | 16.73 |

Synthesis of pMPC-nEGFP, pMPC-nOVA, pMPC-nHRP, pMPC-nGOx, pMPC-nUOx, pMPC-nAOx, pMPC-nTf and pMPC-nBSA After acryloxylation, protein was encapsulated with pMPC using a in situ polymerization method. For the polymerization, 2-Methacryloyloxyethyl phosphorylcholine (MPC) and bis-methacrylamide (BIS) were first prepared as 10% (w/v) stock solution in DI-water and anhydrous DMSO, respectively. Then MPC and BIS were added into the solution of the protein being encapsulated with a specific molar ratio (listed in Table 5). The final protein concentration was tuned to 1 mg/mL by diluting with phosphate buffer (50 mM, pH 7.0). Polymerization was initiated by the addition of ammonium persulfate (APS) and tetramethylethylenediamine (TEMED) and kept at room temperature for 2 h. After the polymerization, the solution was dialyzed against PBS to remove unreacted monomers and by-products. The detailed synthesis parameters of pMPC-nEGFP, pMPC-nOVA, pMPC-nHRP, pMPC-nGOx, pMPC-nUOx, pMPC-nAOx, pMPC-nTf, and pMPC-nBSA were listed in Table 5.

TABLE 5

Synthesis parameters of various pMPC protein nanocapsules

| Sample | Acryloxyl-protein | MPC | BIS | APS | TEMED |
|---|---|---|---|---|---|
| PMPC-nEGFP | 1 | 3000 | 400 | 250 | 500 |
| PMPC-nOVA | 1 | 3000 | 400 | 400 | 800 |
| PMPC-nHRP | 1 | 3000 | 400 | 300 | 600 |
| PMPC-nGOx | 1 | 16000 | 2400 | 800 | 1600 |
| PMPC-nUOx | 1 | 10000 | 1400 | 600 | 1200 |
| PMPC-nAOx | 1 | 80000 | 11000 | 4000 | 8000 |
| PMPC-nTf | 1 | 3000 | 400 | 400 | 800 |
| PMPC-nBSA | 1 | 3000 | 400 | 400 | 800 |

* All numbers indicate molar ratio.

Synthesis of Positively Charged pMPC-nEGFP(+)

The synthesis of positively charged of pMPC-nEGFP(+) is similar as that of pMPC-nEGFP. Instead of using MPC solely as monomer, mixture of MPC and N-(3-Aminopropyl) methacrylamide hydrochloride (APm) with a molar ratio of 9:1 was employed as monomer in the polymerization step. The final molar ratio of monomer to EGFP was kept as 3000:1. After tuning the EGFP concentration to 1.0 mg/mL with phosphate buffer (50 mM, pH 7.0), the polymerization step was initiated using APS/TEMED (1:250:500, EGFP:APS:TEMED, n/n/n), and the reaction was kept at room temperature for 2 h. The reaction solution was then dialyzed against PBS to remove reaction by products.

Synthesis of pAAm-nEGFP, and pAAm-nAOx

The pAAm-nEGFP and pAAm-nAOx are prepared using the method we described before. Here, acrylamide (AAm) was employed as monomer for the encapsulation of EGFP and AOx. Briefly, acryloxyl-EGFP and acryloxyl-AOx were first mixed with AAm and BIS at specific ratios (EGFP:AAm:BIS=1:2000:300, AOx:AAm:BIS=1:50000:7000), respectively. After tuning the protein concentration to 1.0 mg/mL with phosphate buffer (50 mM, pH 7.0), the reactions were initiated using APS/TEMED (EGFP:APS:TEMED=1:250:500, AOx:APS:TEMED=1:4000:8000, n/n/n) respectively, and the reactions were kept at room temperature for 2 h. The reaction solution was then dialyzed against PBS to remove reaction by products.

Synthesis of Positively Charged pAAm-nEGFP(+)

The preparation of positively charged pAAm-nEGFP(+) was achieved with a similar method as the synthesis of pAAm-nEGPF. The mixture of AAm and APm with a molar ratio of 9:1 was employed as monomer for the encapsulation. After mixing the monomers with EGFP, the final molar ratio of EGFP and two monomers is 1:1800:200 (EGFP:AAm:APm). After tuning the protein concentration to 1.0 mg/mL with phosphate buffer (50 mM, pH 7.0), the polymerization step was initiated using APS/TEMED (EGFP:APS:TEMED=1:250:500, n/n/n), and the reactions were kept at room temperature for 2 h. The reaction solution was then dialyzed against PBS to remove reaction by products.

Purification of the Protein Nanocapsules

After dialysis, protein nanocapsules were passed through columns by gravity to remove unencapsulated proteins. Based on the different physical properties, pMPC-based protein nanocapsules and pAAm-based protein nanocapsules were purified with hydrophobic interaction column (Phenyl-Sepharose CL-4B) and size exclusion column (Sepharose-6B), respectively. For the purification of pMPC-nProteins, the column was prepared by pipette 5 mL of Phenyl-Sepharose CL-4B into a glass column. Before loading the sample, the column was pre-equilibrated with 2.5 M sodium sulfate. pMPC-Protein was first mixed with sodium sulfate powder to make the final concentration of sodium sulfate to 2.5 M. Then, the sample was loaded onto the column and eluted with 2.5 M sodium sulfate solution. Since the pMPC-Protein particles possess a super-hydrophilic surface (pMPC), their binding affinity to the column is much weaker than the native protein, especially in such a condition with high salt concentration (2.5 M sodium sulfate). Thus, pMPC-encapsulated protein will eluted with 2.5 M sodium sulfate, whereas the native protein binds on the column. The elution with 2.5 M sodium sulfate was collected and condensed using centrifugal filtration. The sample was then dialyzed against PBS to remove the sodium sulfate, and stored at 4° C. for further studies.

The purification of pAAm-nProteins was achieved using the method we described before. It was achieved by passing sample through a Sepharose-6B column by gravity. Sepharose column was prepared by pipette 5 mL of Sepharose 6B beads into a glass column. The column was then pre-equilibrated with PBS. After equilibration, sample was loaded in the column, and then eluted with PBS. Because the fractionation range of Sepharose-6B is 10,000-4,000,000 Da, encapsulated proteins (pAAm-nProtein) are too big to enter the pores of Sepharose beads, as a result, eluted first during the elution. Eluted solution was collected in a volume of 100 μL per fraction, and the absorbance at 280 nm of each fraction was measured with a UV/Vis meter by using elution buffer (PBS) as background. Fractions of encapsulated proteins (first A280 peak) were collected, combined, and then condensed using centrifugal filtration. Protein nanocomplexes solution was stored at 4° C. for further studies.

Determination of the Protein Concentrations

Protein concentrations of protein nanocapsules, including pMPC-nOVA, pMPC-nEGFP, pMPC-nEGFP(+), pAAm-nEGFP, pAAm-nEGFP(+), pMPC-nHRP, pMPC-nGOx, pMPC-nUOx, pMPC-nAOx, pAAm-nAOx, and pMPC-nTf, were determined using BCA micro-assay. Before tests, two BCA reagents were prepared using the following recipes. Reagent A was prepared by dissolving 0.1 g bicinchoninic acid disodium salt hydrate (BCA), 0.32 g sodium carbonate, 0.01 g tartate acid in 10 mL DI-water, following by tuning the pH to 11.25 with 1 M NaOH solution. Reagent B was prepared by dissolving 0.2 g $CuSO_4 \cdot 5H_2O$ in 5 mL DI-water. BCA working solution (BWS) was prepared by mixing 50 volume of Reagent A and 1 volume of Reagent B together.

Standard curves of each protein were established using native protein with a series of concentrations (0.0078125, 0.015625, 0.03125, 0.0625, 0.125, 0.25, 0.5, 1 mg/mL). This was achieved by repeating 2-fold dilutions of 1 mg/mL protein solution with PBS in a 384-well plate. BCA assays were conducted by adding 10 μL of native protein solutions with different concentrations into each well of 384-well plate respectively, following by the addition of 10 μL of BCA working solution (BWS). In the meanwhile, 10 μL of protein nanocapsule solution was also added into the same plate, following by the addition of 10 μL of BWS. The plate was then incubated at 65° C. for 1 h. Absorbance at 550 nm of each well was read out by using a plate reader. Concentration of the encapsulated protein was calculated by using its absorbance at 550 nm and the standard curve established at the same condition.

TEM and DLS Studies of Protein Nanocapsules

TEM samples were prepared by drop-coating of 2 μL pMPC-nEGFP solution and pMPC-nOVA onto carbon-coated copper grids, respectively. Droplets of samples were contacted with the grids for 45 s, then excess amount of samples was removed with Kimwipes. The grid was then rinsed, and stained with 1% sodium phosphotungstate at pH 7.0. The grid was then rinsed again, followed by the removal of excess staining agent with kimwipes. The grids were dried under vacuum and observed with a FEI Tecnai T12 transmission electron microscope.

DLS Measurements were achieved with a Malvern Zetasizer Nano instrument, with scattering angle at 173'. The particle sizes acquired from DLS were summarized in FIGS. 5A-K.

Activity Assays and Stability of pMPC-nHRP, pMPC-nGOx, pMPC-nUOx, and pMPC-nAOx

The activity of pMPC-nHRP and native HRP were determined by monitoring the oxidation rate of 3,3',5,5'-tetramethylbenzidine (TMB) using hydrogen peroxide ($H_2O_2$) as the substrate. Briefly, a series of $H_2O_2$ stock solutions with concentrations of 0.001%, 0.002%, 0.003%, 0.004%, 0.006%, 0.008% (w/v) was prepared by diluting a 50% $H_2O_2$ (w/v) with 0.1 M acetate buffer (pH 5.01) with 0.5 mM TMB. After mixing 1 mL of the substrate solution with 1 μL of pMPC-nHRP (0.1 mg/mL) or native HRP, the absorbance at 655 nm (A655) of the reaction solution was monitored with a UV-Vis spectrometer for 3 min. The absorption curve was plotted versus time and ΔA655/min from the linear portion of the curve was calculated. The activity assays were repeated with a series of concentrations of substrate to get the catalytic rates to obtain $K_M^{app}$ and $k_{cat}^{app}$ by the Lineweaver—Burk plot.

The activity of native GOx, pMPC-nGOx, native AOx, and pMPC-nAOx were determined with a similar method. Briefly, the initial reaction rates were determined by monitoring the oxidation rates of TMB of GOx and AOx when incubating with the assay solutions with different concentrations of substrates, respectively. For native GOx and pMPC-nGOx, the assay solutions were prepared by mixing TMB (0.5 mM), native HRP (0.001 mg/mL), and different amount of D-gluocose (0.005%, 0.010%, 0.015%, 0.020%, 0.030%, 0.040%, w/v) in 0.1 M phosphate buffer (pH 7.0). For native AOx and pMPC-nAOx, the assay solutions were composed by TMB (0.5 mM), native HRP (0.001 mg/mL), and different amount of ethanol (0.0025%, 0.005%, 0.0075%, 0.010%, 0.020%, 0.030%, w/v) in 0.1 M phosphate buffer (pH 7.0). The measurements were achieved by monitoring the A655 of the reaction solutions during the incubation of 1 μL of native enzyme or pMPC-nProtein (0.5 mg/mL for native GOx and pMPC-nGOx, 1 mg/mL for native AOx and pMPC-nAOx) with their corresponding assay solution.

Native UOx and pMPC-nUOx activities were determined by monitoring the decrease of A290 with UV-spectrometer during the incubation of 1 μL native UOx or pMPC-nUOx (0.714 mg/mL) with a series urate solutions (pH=8, 0.1 M borate buffer, urate concentrations: 0.005%, 0.010%, 0.015%, 0.020%, 0.030%, 0.040%, w/v). The initial rates were achieved by plotting the absorption at 290 nm versus time and calculating the ΔA290/min from the linear portion of the curve.

Thermal stability of native AOx and pMPC-nAOx was conducted using the following procedure: the solutions of native AOx and pMPC-nAOx (1 mg/mL, 10 mM phosphate buffer, pH 7.0) were first incubated at 37° C. for certain periods (1-96 hr), followed by quenching on ice bath and recovering to room temperature. AOx activity assays were then performed with these samples to determine the residual activities of native AOx and pMPC-nAOx.

The stability of native UOx and pMPC-nUOX against protease was conducted using the following protocol: the solutions of native UOx and pMPC-nUOx (0.714 mg/mL, 10 mM borate buffer, pH 8.0, 10 mM $Ca^{2+}$) were mixed with trypsin stock solution (10 mg/mL) to bring the final trypsin concentration to 0.1 mg/mL. The control groups of native UOx and pMPC-nUOx solutions were prepared by mixing the stock solutions with same volume of PBS as that of trypsin solution. The preparation of these four solution were performed in an ice bath to avoid the activation of trypsin. After the preparation, the four solutions were incubated at 37° C. for certain periods (20-180 min), followed by quenching on ice bath. UOx activity assays were then performed with these samples to determined the residual activities of native UOx and pMPC-nUOx.

Cell Viability Assay

The toxicity of pMPC-nProteins, including pMPC-nEGFP, pMPC-nOVA, pMPC-nUOx, and pMPC-nAOx was evaluated by measuring the cell viability after the incubation of U87 cells with different amount of pMPC-nProteins (0.01 mg/mL, 0.05 mg/mL, 0.10 mg/mL, 0.20 mg/mL) for 24 h. For better comparison, the toxicity of native EGFP, OVA, UOx, and AOx were also tested with the same method. U87 cells were seeded into a 96-well plate ($10^4$ cells/well, 100 μL/well) and cultured in DMEM (normal level of glucose in medium, with 10% FBS) for a day prior to exposure to the samples. After the addition of pMPC-nProteins and their native counterparts respectively, cells were further incubated for 24 h. After incubation, CellTiter-Blue (20 μL) was added into each well and further incubated for 3 h. The plate was then placed on a shaking table at 150 rpm for 5 min to thoroughly mix the solution. Viable cells reduce CellTiter Blue and show fluorescent reddish color. Quantification of the cell viability was achieved by measuring the fluorescence intensities with a plate reader (Ex=535 nm, Em=585 nm). The viability of untreated cells was used as 100% during the data analysis.

Cell Uptake of EGFP Protein Nanoparticles with Different Surfaces

To evaluate the effect of surface properties of protein nanocapsules in their cell internalization, we encapsulated EGFP with pAAm and pMPC to get pAAm-nEGFP (zeta potential $\zeta=-3.38$ mV) and pMPC-nEGFP (zeta potential $\zeta=-0.222$ mV) respectively, and also prepared positively charged pAAm-nEGFP(+) (zeta potential $\zeta=+1.27$ mV) and pMPC-nEGFP(+) (zeta potential $\zeta=+1.08$ mV) by introducing APm during the polymerization. The study was achieved by incubating U87 cells with these EGFP nanocapsules. U87 cells were seeded into a 96-well plate ($10^4$ cells/well, 100 μL/well) and cultured in DMEM (normal level of glucose in medium, with 10% FBS) for a day prior to exposure to the samples. EGFP nanocapsules, including pAAm-nEGFP, pAAm-nEGFP(+), pMPC-nEGFP, and pMPC-nEGFP(+), were then added to cells (10 μg/well) and incubated at 37° C. for 4 hrs. After the incubation, cells were rinsed with PBS (1×) for three times to remove the excess samples and culture medium. Fluorescence intensity of the cells were read out using a plate reader (Fujifilm BAS-5000). After the measurement of the fluorescence, the cells were lysed with cell lysis buffer, and the total protein concentration of each well of cells was determined with BCA assay using BSA as standard. The fluorescence intensity of each well was then normalized with the corresponding protein concentration. All the statistical analyses were performed using the Tukey post-test following a one-way ANOVA. $P<0.05$ or less was considered significant.

Engulfment of pMPC-nOVA by Human Blood Peripheral Cells (PBMCs)

Native OVA and pMPC-nOVA were first labeled with rhodamine B for observation and quantification. Human PBMCs were obtained without identifying information from the UCLA Center for AIDS Research (CFAR) Virology Core Laboratory in accordance with UCLA Institutional Review Board (IRB) approved protocols along with an IRB-approved written consent form. PBMCs from 3 donors were isolated from leukopacks by Ficoll 48 hours before transduction. Half of the cells were cultured in RPMI medium, 20% FBS, 1% GPS (L-Glutamine/penicillin/streptomycin) to maintain the quiescent status for 2 days, while the other half were stimulated in RPMI medium, 20% FBS, 1% GPS with 20 units/ml IL-2 and 25 μg/mL PHA for 2 days. PBMCs were plated into a 48-well plate at a density of 1×105 cells per well in Opti-MEM medium. The PBMCs were transduced with PBS, native OVA, and pMPC-nOVA respectively for 4 hrs. The cells were washed in FACS buffer twice and fixed with 2% formaldehyde in PBS. Fluorescent intensity was examined on LSRFortessa (BD Biosciences). The data were analyzed by FlowJo (TreeStar) software. In the live cell gate, lymphocyte population was isolated based on FSC-A vs FSC-H plot and FSC-A vs SSC-A plot. The fluorescent analysis was performed within lymphocyte populations. The rhodamine B positive gate (RhB+) was set based on the PBS treated control sample.

Pharmacokinetics Studies of pMPC-nAOx in Mice

Pharmacokinetics (PK) profiles of native AOx, pAAm-nAOx, and pMPC-nAOx were accessed by monitoring the residual AOx activity in plasma after intravenous administration. Briefly, 12 mice (C57BL/6) were divided into 3 groups and injected with 100 μg of native AOx, pAAm-nAOx, and pMPC-nAOx (1 mg/mL) via tail vein, respectively. As a negative control, another 3 mice were injected with 100 μL of PBS. The blood samples (20 μL) were then taken from the tails at 1 h, 2 h, 4 h, 8 h, 24 h, and 72 h after the injection. The blood samples were then centrifuged at 20 krpm for 5 min to remove the blood cells, and the AOx activity in the plasma was measured using an AOx enzyme activity assay. Residual AOx activities of were determined by incubating 1 μL of plasma with 100 μL of assay solution (1% EtOH, 0.02 mg/mL HRP, and 0.5 mM TMB in 0.1 M phosphate buffer, pH=7.0), and monitoring the absorbance change at 620 nm with a plate reader. A series of native AOx stock solutions with different concentrations (0.4688 μg/mL, 0.9375 μg/mL, 1.875 μg/mL, 3.75 μg/mL, 7.5 μg/mL, 15 μg/mL and 30 μg/mL) were then prepared and used to establish the relationships between reaction rates and AOx concentrations.

The analysis of the PK data was achieved by fitting the data using a two-phase exponential decay model with the constraints of Y0<0.1 (maximum AOx concentration cannot be higher than 0.1 mg/mL) and Plateau=0.005354 (the mean background value from the negative control). All data analysis was achieved using Graphpad Prism.

Biodistribution of pMPC-nEGFP, pMPC-nBSA, pAAm-nBSA, and pAAm-nBSA(+) in Mice

The biodistributions of pMPC-nEGFP, pMPC-nBSA, pAAm-nBSA, and pAAm-nBSA(+) in mice were accessed using Single-photon emission computed tomography (SPECT)/X-ray computed tomography (CT) imaging method. To allow tracing the samples after injection, pMPC-nEGFP, pMPC-nBSA, pAAm-nBSA, and pAAm-nBSA(+) were radioactively labeled with $^{125}$I using the iodogen method before the injection. Samples were then injected into mice (KM) via tail vein at a dosage of 100 μL (~0.1 mg protein) per animal, respectively. Animals were then imaged at 3 h, 24 h, 72 h, 120 h, and 168 h after the administration. For the imaging, animals were first anesthetized with intraperitoneal injection of 100 μL of sodium pentobarbital (2.5%), and then imaged with CT (~7 min on average), following by SPECT scanning (~24 min on average). The details parameters used in CT and SPECT scanning were described as follow. CT: frame resolution, 256×512; tube voltage, 45 kVp; current, 0.15 mA; exposure time, 500 ms/frame. Real-time 3D reconstructions of the collected images were performed using Nucline software (v1.02, Mediso, Hungary). SPECT: for high-resolution, conical collimators with 9-pinhole plates; energy peak, 28 keV; window width, 10%; resolution, 1 mm/pixel; matrix, 256×256; projections, 24; scan time, 60 s/projection. Three-dimensional ordered subset expectation maximization images were reconstructed using HiSPECT (Bioscan, USA). The reconstruction algorithm included four subsets and the sixth-order iterative method, with a resolution of 0.4 mm/pixel.

Immunogenicity Studies of pMPC-nOVA in Mice

Immunogenicity of pMPC-nOVA was accessed by measuring the serum concentration of IgG, IgE, OVA-specific IgG (OVA-sIgG), and OVA-specific IgE (OVA-sIgE) in mice after the injection of pMPC-nOVA. Briefly, 3 groups of mice (BALB/C, 5 animals per group) were administered with PBS (blank control), 100 µg of native OVA (positive control), and 100 µg of pMPC-nOVA (the weight indicates the weight of OVA protein) via tail vein, respectively. Blood samples were then taken from each animal 15-day post injection. The blood samples were then centrifuged to remove the blood cells, and the concentrations of IgE, IgG, OVA-sIgE, OVA-sIgG were determined with ELISA assays.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

The invention claimed is:

1. A method of extending a circulating half-life of a protein, the method comprising:
   conjugating a protein with a vinyl group comprising a polymerizable acryloyl group; and
   encapsulating the protein with a layer of poly(2-methacryloxyloxyethyl phosphorylcholine) (pMPC); wherein:
   the encapsulated protein retains at least 95% of its activity when incubated with 0.1 mg/mL trypsin for at least 90 minutes at 37° C.; and
   the encapsulated protein exhibits an elimination half-life that is at least 2-fold greater than an elimination half-life of the unencapsulated protein;
   such that the circulating half-life of the protein is extended.

2. The method of claim 1, wherein the layer of pMPC comprises a plurality of 2-methacryloxyloxyethyl phosphorylcholine monomers (MPC) polymerized with a N,N'-methylenebisacrylamide (BIS) crosslinker.

3. The method of claim 1, wherein the encapsulated protein retains at least 95% of its activity when incubated with trypsin for at least 90 minutes.

4. The method of claim 1, wherein the encapsulated protein retains at least 90% of its activity when incubated in 37° C. for at least 5 days.

5. The method of claim 1, wherein the encapsulated protein is not coupled to a polyethylene glycol.

6. The method of claim 1, wherein encapsulating the protein with a layer of pMPC delays clearance of the protein by an immune system in vivo.

7. The method of claim 6, wherein encapsulating the protein with a layer of pMPC reduces the protein binding with opsonins, macrophages or antibodies in vivo.

8. The method of claim 1, wherein the layer of pMPC is selected to provide a zwitterionic structure to the encapsulated protein.

9. The method of claim 1, wherein the layer of pMPC has a thickness of 8 to 11 nm.

10. A method of forming a protein nanocapsule, the method comprising:
    conjugating a protein with a vinyl group comprising a polymerizable acryloyl group; and
    encapsulating the protein with a layer of poly(2-methacryloxyloxyethyl phosphorylcholine) (pMPC); such that a protein nanocapsule is formed, wherein:
    the encapsulated protein retains at least 95% of its activity when incubated with 0.1 mg/mL trypsin for at least 90 minutes at 37° C.; and
    the encapsulated protein exhibits an elimination half-life that is at least 2-fold greater than an elimination half-life of the unencapsulated protein.

11. The method of claim 10, wherein the layer of pMPC is formed by polymerizing a plurality of 2-methacryloxyloxyethyl phosphorylcholine monomers (MPC) with a N,N'-methylenebisacrylamide (BIS) crosslinker.

12. The method of claim 10, wherein the layer of pMPC has a thickness of 8 to 11 nm.

13. A composition of matter consisting of:
    a cargo agent; and
    poly(2-methacryloxyloxyethyl phosphorylcholine) (pMPC);
    wherein:
    the pMPC encapsulates the cargo agent;
    the cargo agent is conjugated to pMPC with a vinyl group comprising a polymerizable acryloyl group;
    the encapsulated cargo agent retains at least 95% of its activity when incubated with trypsin for at least 90 minutes; and
    the encapsulated cargo agent exhibits an elimination half-life in vivo that is at least 2-fold greater than an elimination half-life in vivo of the unencapsulated cargo agent.

14. The composition of claim 13, wherein the pMPC comprises a plurality of 2-methacryloxyloxyethyl phosphorylcholine monomers (MPC) polymerized with a N,N'-methylenebisacrylamide (BIS) crosslinker.

15. The composition of claim 13, wherein the layer of pMPC has a thickness of 8 to 11 nm.

16. A method of extending a circulating half-life of a protein, the method comprising:
    conjugating a protein with a polymerizable acryloyl group, wherein the conjugating occurs on lysine residues of the protein; and
    encapsulating the protein with a layer of poly(2-methacryloxyloxyethyl phosphorylcholine) (pMPC); wherein:
    the encapsulated protein retains at least 95% of its activity when incubated with 0.1 mg/mL trypsin for at least 90 minutes at 37° C.; and
    the encapsulated protein exhibits an elimination half-life that is at least 2-fold greater than an elimination half-life of the unencapsulated protein;
    such that the circulating half-life of the protein is extended.

17. A composition of matter consisting of:
    a protein; and
    poly(2-methacryloxyloxyethyl phosphorylcholine) (pMPC);
    wherein:
    the pMPC is conjugated to lysine residues on the protein by a polymerizable acryloyl group; and
    the pMPC encapsulates the protein; wherein:
    the encapsulated protein retains at least 95% of its activity when incubated with 0.1 mg/mL trypsin for at least 90 minutes at 37° C.; and
    the encapsulated protein exhibits an elimination half-life that is at least 2-fold greater than an elimination half-life of the unencapsulated protein.

* * * * *